(12) United States Patent
Hwang et al.

(10) Patent No.: US 11,813,083 B2
(45) Date of Patent: Nov. 14, 2023

(54) ASSEMBLY FOR MEASURING BIO-INFORMATION

(71) Applicant: SAMSUNG ELECTRONICS CO., LTD., Suwon-si (KR)

(72) Inventors: Jeong Eun Hwang, Suwon-si (KR); Byung Hoon Ko, Hwaseong-si (KR); Seung Woo Noh, Seongnam-si (KR); Jong Wook Lee, Suwon-si (KR); Tak Hyung Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 25 days.

(21) Appl. No.: 17/093,013

(22) Filed: Nov. 9, 2020

(65) Prior Publication Data

US 2021/0321884 A1 Oct. 21, 2021

(30) Foreign Application Priority Data

Apr. 21, 2020 (KR) .................. 10-2020-0048023

(51) Int. Cl.
*A61B 5/00* (2006.01)
*A61B 5/318* (2021.01)
(Continued)

(52) U.S. Cl.
CPC ............ *A61B 5/681* (2013.01); *A61B 5/0075* (2013.01); *A61B 5/0077* (2013.01);
(Continued)

(58) Field of Classification Search
CPC . A61B 5/02055; A61B 5/0075; A61B 5/0077; A61B 5/053; A61B 5/1172;
(Continued)

(56) References Cited

U.S. PATENT DOCUMENTS

| | | | |
|---|---|---|---|
| 5,233,404 A | 8/1993 | Lougheed et al. | |
| 6,492,979 B1 * | 12/2002 | Kent | G06F 3/0447 |
| | | | 178/18.05 |
| 10,133,389 B2 | 11/2018 | Shim et al. | |
| 2004/0048665 A1* | 3/2004 | Ogata | A63F 13/06 |
| | | | 463/37 |
| 2010/0036265 A1 | 2/2010 | Kim et al. | |

(Continued)

FOREIGN PATENT DOCUMENTS

| | | |
|---|---|---|
| JP | 3785529 B2 | 6/2006 |
| KR | 10-1764816 A | 8/2017 |

(Continued)

OTHER PUBLICATIONS

Communication dated Jul. 16, 2021 issued by the European Patent Office in counterpart European Application No. 21152043.2.

*Primary Examiner* — Andrey Shostak
(74) *Attorney, Agent, or Firm* — Sughrue Mion, PLLC

(57) ABSTRACT

An assembly for measuring bio-information includes a finger contact interface configured to move based on a contact force applied by a finger of a user to the finger contact interface; a bio-sensor configured to measure the bio-information of the user based on the finger being in contact with the finger contact interface; a force sensor configured to measure the contact force of the finger applied to the finger contact interface; and a support configured to guide movement of the finger contact interface and support the force sensor against the finger contact interface.

17 Claims, 20 Drawing Sheets

(51) Int. Cl.
*A61B 5/0205* (2006.01)
*A61B 5/053* (2021.01)
*A61B 5/1172* (2016.01)
*G06V 40/12* (2022.01)

(52) U.S. Cl.
CPC .......... *A61B 5/02055* (2013.01); *A61B 5/053* (2013.01); *A61B 5/1172* (2013.01); *A61B 5/318* (2021.01); *A61B 5/6802* (2013.01); *A61B 5/6843* (2013.01); *A61B 5/6898* (2013.01); *G06V 40/1359* (2022.01); *G06V 40/1376* (2022.01); *A61B 2562/0252* (2013.01)

(58) Field of Classification Search
CPC ..... A61B 5/318; A61B 5/6802; A61B 5/6843; A61B 5/6898; A61B 2562/0252; A61B 5/6826; A61B 5/02416; A61B 2562/0247; A61B 5/02225; A61B 5/0537; A61B 5/021; A61B 5/02427; A61B 5/28; A61B 5/296; A61B 5/6803; A61B 5/6824; A61B 2560/0406; A61B 5/681; A61B 5/0059; A61B 5/01; A61B 5/332; A61B 5/6844; G06V 40/13; G06V 40/1359; G06V 40/1376
See application file for complete search history.

(56) References Cited

U.S. PATENT DOCUMENTS

| | | |
|---|---|---|
| 2013/0296714 A1* | 11/2013 | Kassim .............. G01N 21/3151 600/479 |
| 2016/0106333 A1 | 4/2016 | Kang et al. |
| 2016/0166162 A1* | 6/2016 | Yamaji ................ A61B 5/6826 600/479 |
| 2016/0270668 A1 | 9/2016 | Gil |
| 2017/0095168 A1 | 4/2017 | Kwon et al. |
| 2017/0340209 A1 | 11/2017 | Klaassen et al. |
| 2018/0184923 A1 | 7/2018 | Tal et al. |
| 2019/0029596 A1 | 1/2019 | Kang et al. |
| 2019/0101870 A1* | 4/2019 | Pandya .................. A61B 5/339 |
| 2020/0064781 A1 | 2/2020 | Shim et al. |
| 2020/0221981 A1* | 7/2020 | Poeze ................. A61B 5/6843 |
| 2020/0288995 A1 | 9/2020 | Hwang et al. |
| 2021/0038098 A1 | 2/2021 | Hwang et al. |

FOREIGN PATENT DOCUMENTS

| | | | |
|---|---|---|---|
| KR | 10-2018-0051227 A | 5/2018 | |
| KR | 10-2020-0110116 A | 9/2020 | |
| KR | 10-2021-0016715 A | 2/2021 | |
| WO | WO-2017214582 A1 * | 12/2017 | ........... A61B 5/1172 |

* cited by examiner

ASSEMBLY FOR MEASURING BIO-INFORMATION

CROSS-REFERENCE TO RELATED APPLICATION(S)

This application claims priority to Korean Patent Application No. 10-2020-0048023, filed on Apr. 21, 2020, in the Korean Intellectual Property Office, the entire disclosure of which is incorporated herein by reference for all purposes.

BACKGROUND

1. Field

Example embodiments of the present disclosure relate to measuring bio-information of a user in a non-invasive manner.

2. Description of Related Art

With the aging population, increased medical costs, and a lack of medical personnel for specialized medical services, research is being actively conducted on technologies in which information technology (IT) and medical technology are combined. Particularly, monitoring of a health condition of a human body may not be limited to places such as hospitals, but is expanded by mobile healthcare fields that may monitor a user's health condition anywhere (e.g., at home, at the office, in transit from one place to another place, or the like) and anytime in daily life.

Some examples of bio-signals, which serve as the user's health indicators, may include an electrocardiography (ECG) signal, a photoplethysmogram (PPG) signal, an electromyography (EMG) signal, and the like, and various bio-information measurement devices are being developed to measure the bio-signals in daily life. For example, the bio-information measurement device may be configured to measure a user's bio-signals in a state in which the user's finger is in contact with an interface, thereby non-invasively measuring the bio-signals and estimating a health indicator.

If such a bio-information measurement device is mounted in a wearable device, a mobile device, or the like, various bio-signals may be non-invasively measured and be utilized in the mobile healthcare fields. To this end, the bio-information measurement device should be miniaturized and configured to increase measurement accuracy while being applicable to various electronic devices, such as wearable devices and mobile devices.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an example embodiment, an assembly for measuring bio-information includes a finger contact interface configured to be actuated based on a contact force applied by a finger of a user to the finger contact interface; a bio-sensor configured to measure the bio-information of the user based on the finger being in contact with the finger contact interface; a force sensor configured to measure the contact force of the finger applied to the finger contact interface; and a support configured to guide movement of the finger contact interface and support the force sensor against the finger contact interface.

The support comprises a guide hole through which a part of the finger contact interface is inserted, and that is configured to linearly guide the movement of the finger contact interface.

The finger contact interface comprises an interface body configured to contact the finger of the user on a first side of the interface body; and an interface shaft having a smaller cross-sectional area than the interface body, and that is configured to protrude from a second side of the interface body and move linearly within the guide hole of the support.

At least one force sensor is disposed around a periphery of the guide hole of the support, and faces the interface body.

The finger contact interface comprises a position guide part configured to guide a position of the finger.

The finger contact interface comprises a non-slip part configured to reduce slippage of the finger in contact with the finger contact interface.

The bio-sensor comprises a light receiver mounted on the support, and that is configured to receive light reflected from an irradiated tissue of the finger in contact with the finger contact interface.

The finger contact interface comprises a light path part formed in a shape that widens as the light path part extends away from the light receiver.

The assembly further comprises a processor configured to estimate the bio-information of the user based on a first signal received from the light receiver and a second signal received from the force sensor.

The light receiver comprises a photodetector mounted on the support; a lens configured to collect incident light and transmit the incident light to the photodetector; and an optical filter configured to receive the incident light and pass light of a specific wavelength range to the photodetector.

The photodetector is an image sensor.

The assembly further comprises a processor configured to identify the user by acquiring fingerprint information of the user based on a signal received from the image sensor.

The bio-sensor comprises a light emitter mounted on the finger contact interface, and that is configured to emit light to a tissue of the finger in contact with the finger contact interface.

The light emitter comprises a light source mounted on the finger contact interface; and a light diffusion member configured to diffuse light emitted from the light source.

The bio-sensor comprises an electrode configured to measure at least one of a bio-impedance and an electrocardiogram by contacting the finger through the finger contact interface.

The bio-sensor comprises a temperature sensor configured to measure a temperature signal of the finger in contact with the finger contact interface.

According to an aspect of an example embodiment, an assembly for measuring bio-information may comprise a finger contact interface configured to be actuated based on a contact force applied by a finger of a user to the finger contact interface; a bio-sensor configured to measure the bio-information of the user based on the finger being in contact with the finger contact interface; a force sensor configured to measure the contact force of the finger applied to the finger contact interface; and a support formed on a frame of an electronic device, and that is configured to guide movement of the finger contact interface and support the force sensor against the finger contact interface.

The bio-sensor comprises a light emitter mounted on the electronic device, and that is configured to emit light to a tissue of the finger in contact with the finger contact interface; and a light receiver mounted on the support, and that is configured to receive light reflected from the tissue of the finger in contact with the finger contact interface.

The assembly further comprises a processor configured to estimate the bio-information of the user based on a first signal received from the light receiver and a second signal received from the force sensor; and control a display of the electronic device to display an estimation result.

The electronic device is one of a wearable device and a mobile device.

Other features and aspects will be apparent from the following detailed description, the drawings, and the claims.

BRIEF DESCRIPTION OF THE DRAWINGS

The above and other aspects, features, and advantages of certain example embodiments of the present disclosure will be more apparent from the following description taken in conjunction with the accompanying drawings, in which.

DETAILED DESCRIPTION

Figure 1:
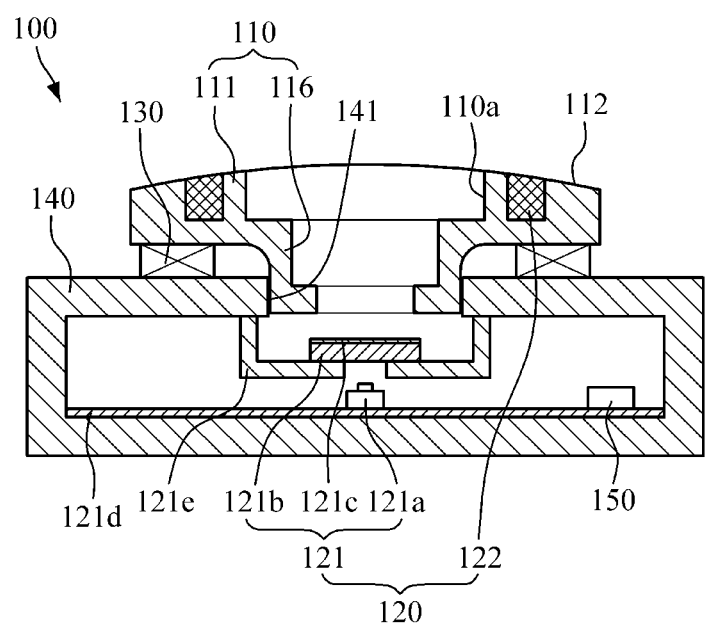
FIG. 1 is a cross-sectional view illustrating an assembly for measuring bio-information according to an example embodiment.

Details of example embodiments are provided in the following detailed description with reference to the accompanying drawings. The disclosure may be understood more readily by reference to the following detailed description of example embodiments and the accompanying drawings. The disclosure may, however, be embodied in many different forms and should not be construed as being limited to the example embodiments set forth herein. Rather, these example embodiments are provided so that the disclosure will be thorough and complete and will fully convey the inventive concept of the disclosure to those skilled in the art, and the disclosure will be defined by the appended claims. Like reference numerals refer to like elements throughout the specification.

Throughout the drawings and the detailed description, unless otherwise described, the same drawing reference numerals will be understood to refer to the same elements, features, and structures. The relative size and depiction of these elements, features, and structures may be exaggerated for clarity, illustration, and convenience.

It will be understood that, although the terms "first," "second," etc. may be used herein to describe various elements, these elements should not be limited by these terms. These terms are used to distinguish one element from another. Also, the singular forms of terms are intended to include the plural forms of the terms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as "unit" and "module" denote units that process at least one function or operation, and they may be implemented by using hardware, software, or a combination of hardware and software.

As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Hereinafter, example embodiments of an assembly for measuring bio-information will be described in detail with reference to the drawings.

Figure 2:
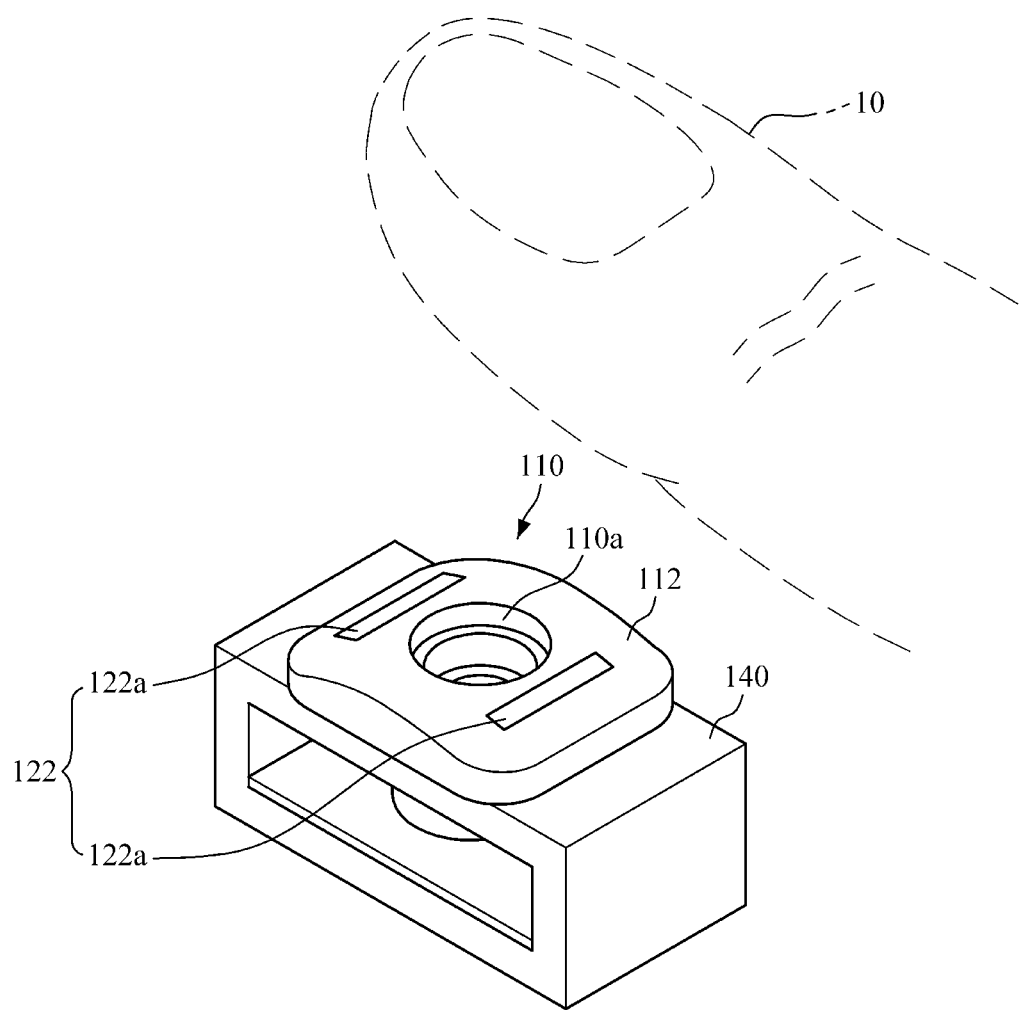
FIG. 2 is a perspective view of FIG. 1.
Figure 3:
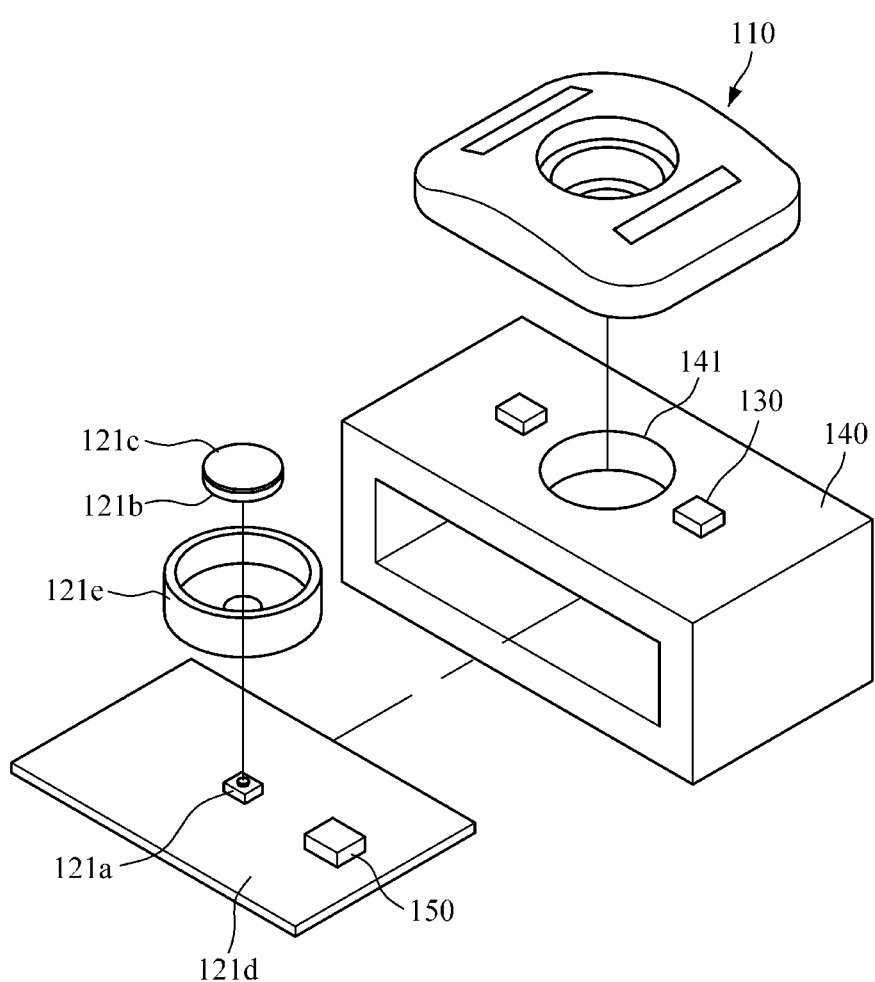
FIG. 3 is an exploded perspective view of FIG. 2.
Figure 4:
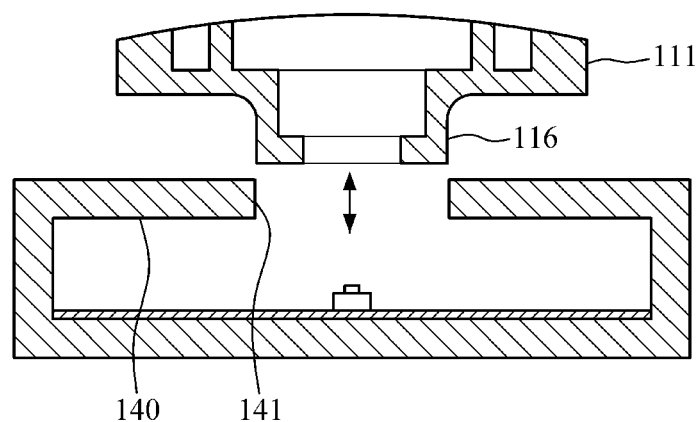
FIG. 4 is a cross-sectional view for describing an action of a finger contact interface and a support.

FIG. 1 is a cross-sectional view illustrating an assembly for measuring bio-information according to an example embodiment. FIG. 2 is a perspective view of FIG. 1. FIG. 3 is an exploded perspective view of FIG. 2. FIG. 4 is a cross-sectional view for describing an action of a finger contact interface and a support.

Referring to FIGS. 1 to 4, an assembly 100 for measuring bio-information according to an example embodiment includes a finger contact interface 110, a bio-sensor 120, a force sensor 130, and a support 140.

The finger contact interface 110 is actuated based on a contact force applied by a finger 10 of a user in contact with the finger contact interface 110. The bio-sensor 120 measures a bio-signal of the user while the finger contact interface 110 is in contact with the finger 10. The force sensor 130 measures a contact force of the finger 10 applied to the finger contact interface 110. The support 140 guides the movement of the finger contact interface 110 while supporting the force sensor 130 against the finger contact interface 110.

In the assembly 100 for measuring bio-information, the force sensor 130 is interposed between the finger contact interface 110 and the support 140. That is, based on the finger contact interface 110 disposed above the support 140, the force sensor 130 measures the contact force of the finger contact interface 110 while being disposed on an upper part of the support 140 in a manner to face a portion of the finger contact interface 110.

As described above, in the present example embodiment, the force sensor 130 may be interposed between the finger contact interface 110 and the support 140 and measures the contact force of the finger contact interface 110, so that the height of the assembly 100 for measuring bio-information can be reduced as compared to a comparative example in which the force sensor 130 is disposed on a lower part of the support 140 and measures the contact force of the finger contact interface 110. Therefore, the assembly 100 for measuring bio-information according to the present example embodiment is more compact and applicable to various electronic devices.

In addition, in the present example embodiment, the force sensor 130 is mounted on the finger contact interface 110 and directly measures the contact force of the finger contact interface 110, so that loss of the contact force measured can be minimized (or reduced) as compared to a comparative example in which the force sensor 130 is disposed on the lower part of the support 140 and indirectly measures the contact force of the finger contact interface 110 via the support 140.

Further, in the comparative example, the force sensor 130 is mounted on the lower part of the support 140, and hence there is a high possibility of measurement error of the force sensor 130 due to structural influences of the support 140, such as the shape of the support 140 and the center of the mass. In contrast, in the present example embodiment, the force sensor 130 is directly mounted on the finger contact interface 110, and hence the measurement error of the force sensor 130 may be reduced as compared to the comparative example. As a result, compared to the comparative example, the present example embodiment can improve measurement accuracy of the force sensor 130.

The finger contact interface 110 may have a level of strength that prevents (or reduces) deformation when pressed by the finger 10. The finger contact interface 110 may be made of a high-strength plastic material with a strength of 0.5 GPa or greater. The finger contact interface 110 may have a maximum transverse length of 12 mm, a maximum longitudinal length of 12 mm, and a maximum height of 10 mm.

The finger contact interface 110 may include an interface body 111 and an interface shaft 116. The interface body 111 is in contact with the user's finger 10 on one side thereof. The interface body 111 has a quadrangular circumference, and the other portion may be formed in a flat shape.

The interface body 111 has a finger contact surface 112 on one side thereof. The finger contact surface 112 may be formed as a smooth surface. The finger contact surface 112 may be formed in a convexly curved shape along a transverse direction or longitudinal direction. When the finger contact surface 112 forms a curved surface, a deeper deformation of the finger 10 may be made when the finger 10 is pressed with the same force, as compared to the case where the finger contact surface 112 forms a flat surface.

Accordingly, it is possible for the user to produce the same deformation of the finger by applying less force to the finger contact surface 112. Alternatively, the finger contact surface 112 may be formed in a planar shape or a concave shape. In addition, the interface body 111 may have a shape having a circular circumference.

The interface shaft 116 may have a smaller cross-sectional area than that of the interface body 111, and protrude from the other side of the interface body 111. The interface shaft 116 may be integrally made of the same material as the interface body 111.

The interface shaft 116 may extend and protrude from the center of the other side of the interface body 111 to have a certain outer circumference size. The outer circumference of the interface shaft 116 may be circular. The interface shaft 116 may have various outer circumferential shapes, such as a quadrangular outer circumference.

The support 140 may include a guide hole 141 through which a part of the finger contact interface 110, for example, the interface shaft 116, is inserted, thereby linearly guiding the movement of the finger contact interface 110. The guide hole 141 has the same shape as the outer circumferential shape of the interface shaft 116. For example, when the outer circumference of the interface shaft 116 is circular, the guide hole 141 is formed in a circular shape.

The interface shaft 116 is linearly movably inserted into the guide hole 141 of the support 140. Accordingly, when the interface body 111 is pressed by the finger 10 or released from the pressed state, the interface shaft 116 linearly moves through the guide hole 141 of the support 140, so that the finger contact interface 110 can stably move linearly with respect to the support 140. Therefore, the finger contact interface 110 presses the force sensor 130 while linearly moving without tilting when pressed by the finger 10, and thus the measurement accuracy of the force sensor 130 can be improved.

An outer surface of the interface shaft 116 and an inner surface of the guide hole 141 may each have a surface roughness that enables a smooth sliding therebetween. For example, based on the Korean Industrial Standards (KS), the outer surface of the interface shaft 116 and the inner surface of the guide hole 141 may have a finish level of 1.6 or less in center-line average roughness (Ra), 6.3 S or less in maximum height roughness (Ry), and 6.3 z or less in 10-point average roughness (Rz).

At least one force sensor 130 may be disposed at a periphery of the guide hole 141 of the support 140 to face the interface body 111. Accordingly, the force sensor 130 may measure the contact force of the finger contact interface 110 while being supported by the support 140. In this case, the support 140 may have a level of strength that prevents the support 140 from deforming due to the contact force of the finger contact interface 110 transmitted through the force sensor 130. The support 140 may be made of a high-strength plastic material with a strength of 0.5 GPa or greater.

The force sensor 130 may be provided as a pair of force sensors that are symmetrically disposed around the guide hole 141. Accordingly, the force sensors 130 may accurately measure the contact force of the finger contact interface 110. Alternatively, three or more force sensors 130 may be arranged around the guide hole 141 at equal intervals.

The force sensor 130 may be in a miniaturized form and be easily applied between the finger contact interface 110 and the support 140. The force sensor 130 may be formed as a strain gauge or a piezo sensor. The force sensor 130 may measure the contact force of the finger contact interface 110 according to the displacement. The force sensor 130 may have a smaller transverse length and longitudinal length than the finger contact interface 110 and may have a maximum height of 1 mm or less.

The bio-sensor 120 may include a light receiver 121. The light receiver 121 is mounted in the support 140 to receive light reflected from the finger tissue in contact with the finger contact interface 110. The support 140 may have an inner space formed to communicate with the guide hole 141. The light emitter 122 may be accommodated in the inner space of the support 140.

The light receiver 121 may include a photodetector 121a, a lens 121b, and an optical filter 121c. The photodetector 121a is mounted on the support 140. The photodetector 121a may be formed as a photodiode, an image sensor, or the like. One photodiode or an array of a plurality of photodiodes may be provided. The image sensor may be a complementary metal oxide semiconductor (CMOS) image sensor (CIS), or the like.

The photodetector 121a may be mounted on a circuit substrate 121d and fixed to an inner wall of the support 140 while facing the guide hole 141 of the support 140. The photodetector 121a may be positioned to correspond to the center of the guide hole 141. Alternatively, the photodetector 121a may be disposed away from the guide hole 141 and at an edge of the support 140 as necessary, or may be provided in plural.

The lens 121b collects incident light and transmits the incident light to the photodetector 121a. The lens 121b adjusts a focal distance for the photodetector 121a and secures a field of view (FOV) and an amount of light. The lens 121b may be formed as a micro lens having a diameter of 6 mm or less and a working distance of 10 mm or less.

The lens 121b may be supported inside a barrel 121e. The barrel 121e has an inner space, a top opening, and a bottom opening. The barrel 121e accommodates and fixes the lens 121b in a state in which the respective centers of the top opening and the bottom opening coincide with the optical axis of the lens 121b. Accordingly, the barrel 121e may pass the incident light through the lens 121b inside thereof and transmit the incident light to the photodetector 121a. The barrel 121e may be fixed in the inner space of the support 140 in a state in which the top opening and the bottom opening correspond to the guide hole 141 of the support 140.

The optical filter 121c receives the incident light and passes light of a specific wavelength range through to the photodetector 121a. The optical filter 121c blocks external light of wavelengths other than a specific wavelength range. For example, a light source 122a of 855 nm emits light to the tissue of the finger 10 in contact with the finger contact interface 110, a filter that cuts off light of 600 nm or less may be used as the optical filter 121c.

The optical filter 121c may be disposed in front or rear of the lens 121b with respect to a direction of the incident light passing through the lens 121b. The optical filter 121c may be mounted on the lens 121b, or on the photodetector 121a. The optical filter 121c may be configured integrally with the image sensor-type photodetector 121a.

The finger contact interface 110 may include a light path part 110a. The light path part 110a may transmit light reflected from the tissue of the finger 10 in contact with the finger contact interface 110 so that the transmitted light can be detected by the photodetector 121a. The light path part 110a may be formed in a shape that extends as it extends farther away from the light receiver 121. Accordingly, the light path part 110a increases the angle of field while miniaturizing the assembly 100 for measuring bio-information, which allows the photodetector 121a to obtain a greater amount of information of a measurement site.

The light path part 110a may widen in a stepwise manner to form a stair-shape as it extends farther away from the light receiver 121. The light path part 110a may have stepwise increasing circumferences in a circular shape. The stepwise increasing circumferences of the light path part 110a may form concentric circles. The finger contact interface 110 may be made of a non-light-transmissive material, and the light path part 110a may be formed as a hole in the finger contact interface 110. Accordingly, the finger contact interface 110 transmits light only through the light path part 110a.

The light path part 110a in the form of a hole may have a transparent member provided thereto or be filled with a transparent material to block foreign substances. In another example, the light path part 110a may be formed in a shape that gradually widens without steps as it extends farther away from the light receiver 121, such that the light path part 110a is not limited to the above examples.

A signal received from the light receiver 121 may be provided to a processor 150 along with a signal received from the force sensor 130. The processor 150 may estimate bio-information of the user on the basis of the signal received from the light receiver 121 and the signal received from the force sensor 130. When the assembly 100 for measuring bio-information includes the processor 150, the assembly 100 is applicable to a wearable device, such as eyeglasses, in which the processor 150 is not mounted.

The processor 150 may estimate bio-information, such as mean blood pressure, systolic blood pressure (SBP), diastolic blood pressure (DBP), a vascular age, arterial stiffness, an aortic artery pressure waveform, a vascular elasticity, a stress index, and a fatigue level. Hereinafter, blood pressure will be taken as an example for the convenience of description.

The light receiver 121 may measure a PPG signal of the user. The PPG signal is a waveform that reflects the change in vascular volume in peripheral parts according to the heartbeat. The blood that is released from the left ventricle in the systolic phase is transferred to the peripheral tissues, so the blood volume of the artery is increased.

Red blood cells carry more oxyhemoglobin to the peripheral tissues in the systolic phase of the heart. In the diastolic phase, the blood partially flows from the peripheral tissues into the heart. When light is emitted to the peripheral veins, the light is absorbed by the peripheral tissues.

The light absorbance is dependent on hematocrit and the blood volume. The light absorbance has a maximum value in the systolic phase of the heart, and has a minimum value in the diastolic phase of the heart. The PPG signal reflects the maximum value of the light absorbance in the systolic phase of the heart, and reflects the minimum value of the light absorbance in the diastolic phase of the heart. In addition, the PPG signal may appear to oscillate with the heart cycle period. Therefore, the PPG signal reflects the change of blood pressure according to the heartbeat, and thus it can be used for blood pressure measurement.

The processor 150 may obtain the user's blood pressure by analyzing the PPG signal according to the contact pressure. A signal output from the photodetector 121a may be processed by a signal processor dedicated for the bio-sensor and then provided to the processor 150. Based on receiving the PPG signal from the photodetector 121a, the signal processor dedicated for the bio-sensor may perform processing, such as noise removal from the received signal, signal amplification, or the like, and when the received signal is an analog signal, may convert the received signal into a digital signal.

A signal output from the force sensor 130 may be processed by a signal processor dedicated for the force sensor and provided to the processor 150. Based on receiving the signal from the force sensor 130, the signal processor dedicated for the force sensor may perform processing, such as noise removal from the signal, signal amplification, or the like, and when the received signal is an analog signal, may convert the received signal into a digital signal.

The processor 150 may calculate a contact pressure by dividing the contact force value measured by the force sensor 130 by the contact area value of the finger contact interface 110. The contact area value of the finger contact interface 110 corresponds to the area of the finger contact surface 112. The processor 150 may estimate blood pressure using oscillometry based on the contact pressure and a maximum peak point of the PPG signal.

For example, the processor 150 may acquire a mean arterial pressure (MAP) on the basis of the contact pressure corresponding to a point in time of the maximum peak point. In addition, the processor 150 may acquire SBP and DBP on the basis of contact pressures at the right and left points in time at each of which an amplitude has a value equal to a preset peak percentage (within a range of 0.5 to 0.7) of the amplitude of the maximum peak point. In this case, the processor 150 may estimate blood pressure by using an estimation model, such as a mathematical function that defines a correlation between extracted features and/or contact pressures and blood pressure.

When the photodetector 121a is an image sensor, the processor 150 may identify the user by acquiring fingerprint information of the user on the basis of a signal received from the image sensor. The processor 150 may obtain the fingerprint information by analyzing valley and ridge patterns of the fingerprint through image processing. The processor 150 may identify the user by comparing the fingerprint information acquired from the image sensor with pre-input fingerprint data.

The processor 150 may store the blood pressure information measured from the user as user information in a storage. The user's blood pressure may be corrected based on height, weight, age, and the like. For example, the processor 150 may correct blood pressure according to the pre-input height, weight, and age information of the user. A blood pressure estimation correlation model suitable for each user may be stored in the storage in advance, and the processor 150 may correct blood pressure by selecting a blood pressure estimation correlation model, which is suitable for a corresponding user, from the storage.

The bio-sensor 120 may include a light emitter 122. The light emitter 122 may be mounted in the finger contact interface 110 to emit light to the tissue of the finger 10 in contact with the finger contact interface 110. The light emitter 122 may include at least one light source 122a. The light source 122a may be mounted in the finger contact interface 110.

The light source 122a may include a light emitting diode, a laser diode, or the like, but is not limited thereto. The light source 122a may be configured to emit light in a wavelength range of 400 nm to 1000 nm. The processor 150 may control the driving of the light source 122a.

A pair of light sources 122a may be mounted on the finger contact surface 112 to be symmetrical with respect to the light path part 110a of the finger contact interface 110. In this case, the light sources 122a may be mounted by being inserted into mounting grooves of the finger contact surface 112. When a camera flash is provided in the electronic device on which the assembly 100 for measuring bio-information is mounted, the light emitter 122 may be omitted from the finger contact interface 110.

Figure 5:
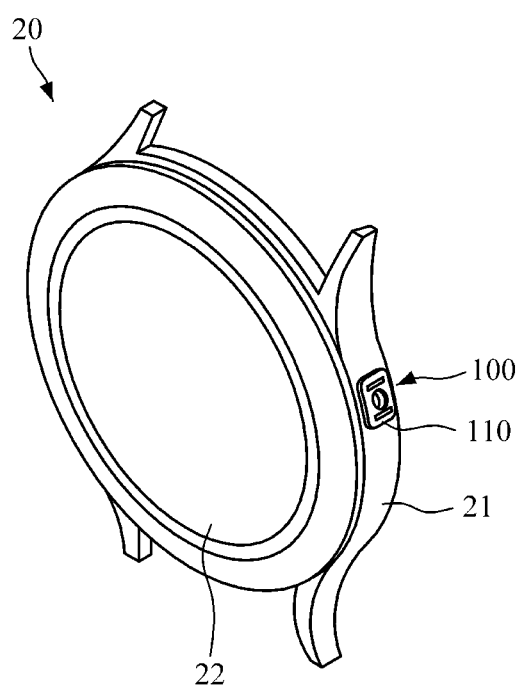
FIG. 5 is a perspective view illustrating an example in which the assembly for measuring bio-information according to an example embodiment is applied to an electronic device.
Figure 6:
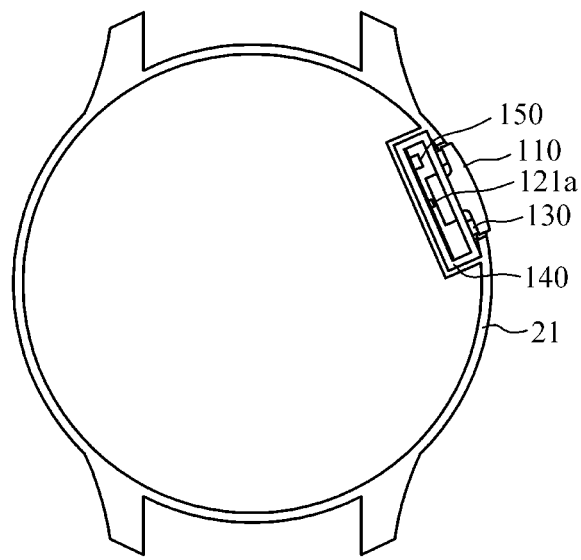
FIG. 6 is a partial cross-sectional view of FIG. 5.

FIG. 5 is a perspective view illustrating an example in which the assembly for measuring bio-information according to an example embodiment is applied to an electronic device. FIG. 6 is a partial cross-sectional view of FIG. 5.

Referring to FIGS. 5 and 6, the assembly 100 for measuring bio-information may be applied to an electronic device, for example, a smartwatch 20. The assembly 100 for measuring bio-information may be accommodated in the smartwatch 20 with the finger contact interface 110 exposed through a hole of the frame 21 of the smartwatch 20, and the support 140 may be fixed to the frame 21 of the smartwatch 20.

The processor 150 may estimate the user's bio-information based on signals received from the bio-sensor 120 and the photodetector 121a and a signal received from the force sensor 130, and display the estimation result on a display 22 of the smartwatch 20.

For example, a process of measuring blood pressure using the smartwatch 20 to which the assembly 100 for measuring bio-information is applied may be performed as described below. First, the user executes a measurement program through an input interface or the like of the smartwatch 20. Then, the force sensor 130 is prepared and on standby through calibration, or the like. In this state, the user presses the finger contact interface 110 with a finger for several seconds or several tens of seconds.

Then, the processor 150 identifies a position of the finger and acquires a PPG signal on the basis of information provided through the photodetector 121a. The processor 150 may estimate blood pressure on the basis of the acquired PPG signal, and then display the estimation result on the display 22 of the smartwatch 20.

Figure 7:
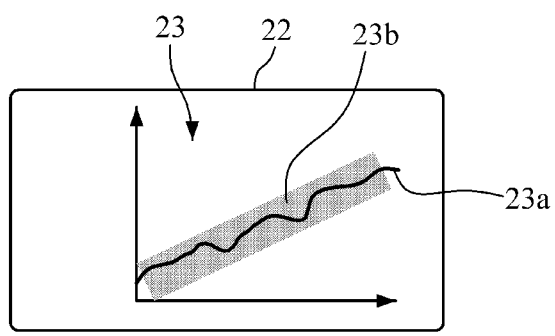
FIG. 7 is a diagram illustrating an example of pressure guide information displayed on a display.

As shown in FIG. 7, when the finger is pressed against the finger contact interface 110, the display 22 may display pressure guide information 23 to guide the user to change a contact pressure between the finger and the finger contact interface 110.

For example, the pressure guide information 23 may include information regarding a reference contact pressure 23b to induce a gradual increase of the contact pressure 23a while the finger is in contact with the finger contact interface 110 or, alteratively, to induce a gradual reduction of the contact pressure 23a while the contact pressure 23a greater than or equal to a predetermined initial threshold is being applied to the finger contact interface 110. In this case, the information regarding the reference contact pressure 23b may include a reference contact pressure value at each point in time or a range of a reference contact pressure.

In this way, the user is able to touch the finger contact interface 110 with a finger while paying attention to the pressure guide information 23 to ensure that the contact pressure 23a does not deviate from the range of the reference contact pressure 23b according to the pressure guide information 23 displayed on a screen of the display 22. As a result, more accurate blood pressure measurement may be performed.

The display 22 may provide additional information, such as a warning or an alarm, in addition to the blood pressure information, to the user by displaying the information. For example, when a dangerous level of blood pressure is extracted, it may be displayed in red color, and alternatively, when a normal level of blood pressure is extracted, it may be displayed in green color.

The display 22 may include a touch input function, by which the user may input various commands, and the display 22 may output a user interface for performing various operations.

Figure 8:
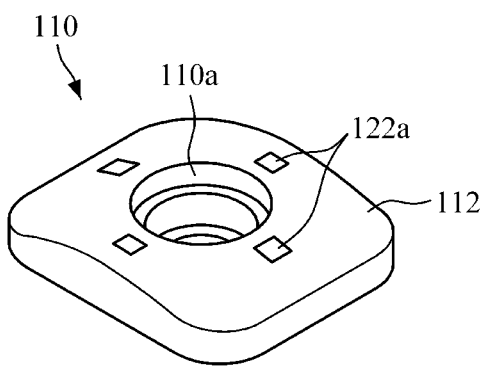
FIG. 8 is a perspective view illustrating another example of a light emitter.

FIG. 8 is a perspective view illustrating another example of a light emitter.

Referring to FIG. 8, the light sources 122a may be arranged in a circle along an entrance of the light path part 110a, and mounted on the finger contact surface 112. The light sources 122a may be arranged at equal intervals with respect to each other to emit light evenly along the periphery of the light path part 110a.

Figure 9:
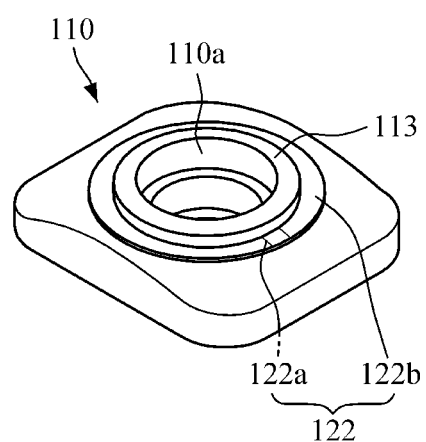
FIG. 9 is a perspective view illustrating still another example of a light emitter.

FIG. 9 is a perspective view illustrating still another example of a light emitter.

Referring to FIG. 9, the light emitter 122 may include one light source 122a and a light diffusion member 122b. The light source 122a is mounted on the finger contact surface 112 of the finger contact interface 110. The light diffusion member 122b diffuses light emitted from the light source 122a. The light diffusion member 122b enables light to be distributed in various directions while minimizing (or reducing) the number of light sources 122a.

The light diffusion member 122b may be formed in a shape that surrounds the entrance of the light path part 110a in a circular shape with a uniform width, for example, in the shape of a circular band. The light diffusion member 122b may be disposed to cover the light source 122a. The light diffusion member 122b may allow the light emitted from the light source 122a to be distributed in a circular form so that the photodetector 121a can acquire a bio-signal in various directions. The light diffusion member 122b, which is in the form of a film, may be attached to the finger contact surface 112 of the finger contact interface 110. As described above, a plurality of light sources 122a may be arranged in a circle along the periphery of the entrance of the light path part 110a and emit light to the light diffusion member 122b.

The finger contact surface 112 may be provided with a partition wall 113 between the light emitter 122 and the light path part 110a. The partition wall 113 is made of a non-light-transmissive material. Therefore, the partition wall 113 blocks the light emitted from the light emitter 122 from directly entering the light receiver 121. The partition wall 113 protrudes from the finger contact surface 112 along the periphery of the entrance of the light path part 110a to form a circular shape with a uniform width. The partition wall 113 may be integrally made of the same material as the finger contact interface 110.

In another example, the finger contact surface 112 may have a circular band-shaped recessed groove concentric with the entrance of the light path part 110a, thereby forming the partition wall 113 around the entrance of the light path part 110a. The light diffusion member 112b may be accommodated and attached to the recessed groove of the finger contact surface 112. Accordingly, the partition wall 113 may be positioned higher than the light diffusion member 122b to prevent the emitted light from directly entering the light receiver 121.

Figure 10:
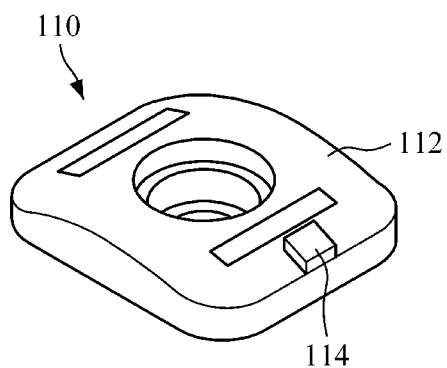
FIG. 10 is a perspective view illustrating an example in which a position guide part is provided in a finger contact interface.

FIG. 10 is a perspective view illustrating an example in which a position guide part is provided in a finger contact interface.

Referring to FIG. 10, the finger contact interface 110 may include a position guide part 114 to guide a position of the finger 10. The position guide part 114 may guide the user to consistently touch at the same position with the finger 10 whenever the user measures a bio-signal at different time periods, thereby improving the reproducibility of the bio-signal. A touch at the same position may include a finger's touch at a position within an allowable range for a set position of the finger contact surface 112.

The position guide part 114 may be formed on the finger contact surface 112 to provide a tactile sensation to the finger 10 while in contact with the finger contact surface 112. The position guide part 114 may be disposed on an edge of the finger contact surface 112. The position guide part 114 may have a convex shape protruding from the finger contact surface 112. The position guide part 114 may be integrally made of the same material as the finger contact interface 110.

As the size of the position guide part 114 increases, tactile perception may become stronger, but a feeling of pressure applied to the finger 10 may increase. As the size of the position guide part 114 decreases, tactile perception may weaken, but a feeling of pressure applied to the finger 10 may decrease. Therefore, the position guide part 114 may be formed in a size that compromises the tactile perception and the feeling of pressure.

The position guide part 114 may be formed in various shapes, such as a hexagonal column, a hemisphere, a dome, or the like, in a range that allows tactile perception. The position guide part 114 may be provided in plural. In addition, the position guide part 114 may be formed in a concave shape.

Figure 11:
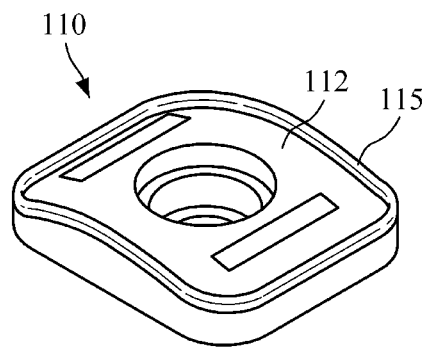
FIG. 11 is a perspective view illustrating an example in which a non-slip part is provided in a finger contact interface.

FIG. 11 is a perspective view illustrating an example in which a non-slip part is provided in a finger contact interface.

Referring to FIG. 11, a finger contact interface 110 may include a non-slip part 115 to prevent slipping of a finger 10 in contact with a finger contact interface 110. The non-slip part 115 may be formed to have an uniform width along an edge of the finger contact surface 112. The non-slip part 115 may be made of a rubber material that increases friction, or a material having a high surface roughness, in the shape of a strip and may be attached along the edge of the finger contact surface 112. In another example, the non-slip part 115 may be processed to have a high surface roughness along the edge of the finger contact surface 112. The non-slip part 115 may also function to guide a position of the finger 10.

Figure 12:
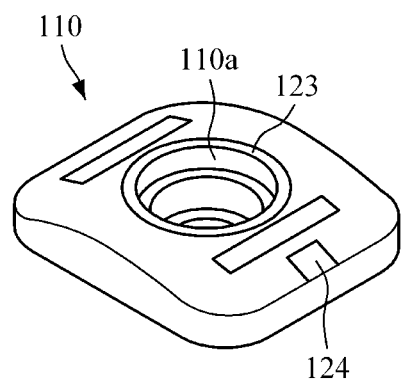
FIG. 12 is a perspective view illustrating an example in which an electrode and a temperature sensor are provided in a finger contact interface.

FIG. 12 is a perspective view illustrating an example in which an electrode and a temperature sensor are provided in a finger contact interface.

Referring to FIG. 12, a bio-sensor 120 may include an electrode 123 to measure at least one of a bio-impedance and an electrocardiogram by contacting a finger 10 through a finger contact interface 110. The electrode 123 may be mounted on a finger contact surface 112 to be externally exposed. The electrode 123 may be made of a conductive metal material in the shape of a strip and be attached to the finger contact surface 112 along a periphery of a light path part 110a. However, the electrode 123 may be provided in various shapes and numbers and be attached to the finger contact surface 112.

When a bio-impedance is measured, the electrode 123 may apply a current signal to the finger 10 in contact with the electrode 123, and allow a voltage signal to be detected from the finger 10. The processor 150 may apply a current to the electrode 123 so that the current signal can be applied to the finger 10, and the processor 150 may measure a bio-impedance by analyzing the voltage signal detected from the electrode 123.

The processor 150 may estimate bio-information, such as a ratio of a body tissue, for example, body fat or the like, on the basis of the measured bio-impedance. The processor 150 may estimate bio-information by using an estimation model, such as a mathematical function that defines a correlation between the measured bio-impedance and the bio-information.

When an electrocardiogram is measured, the electrode 123, which is in contact with the finger 10, may enable a minute electrical signal to be detected from the skin of the finger 10 for each heartbeat. At a resting phase, each cardiac muscle cell has a negative charge. These negative charges are decreased due to the inflow of cations, and thus the depolarization occurs and the heart contracts. During each heartbeat, the heart provides an orderly depolarization wave form spreading out from the signal coming out from a sinoatrial node to whole ventricle.

The electrical signal detected from the electrode 123 may be provided to the processor 150. The processor 150 may measure an electrocardiogram by analyzing the electrical signal detected from the electrode 123. The processor 150 may measure the electrocardiogram by using an estimation model, such as a mathematical function that defines a correlation between the detected electrical signal and the electrocardiogram.

In addition, the bio-sensor 120 may include a temperature sensor 124 to measure a temperature signal of the finger 10 in contact with the finger contact interface 110. The temperature sensor 124 may be mounted on the finger contact surface 112. The temperature sensor 124 may be formed by a thermocouple or the like. A signal output from the temperature sensor 124 may be provided to the processor 150.

A PPG signal may be affected by temperature. In this case, the processor 150 may correct a PPG signal according to a temperature signal measured from the temperature sensor 124. The processor 150 may correct the PPG signal according to the temperature signal by using a correlation model that represents a correlation between a pre-input temperature and a PPG signal. Accordingly, the processor 150 may acquire more accurate blood pressure on the basis of the corrected PPG signal.

Figure 13:
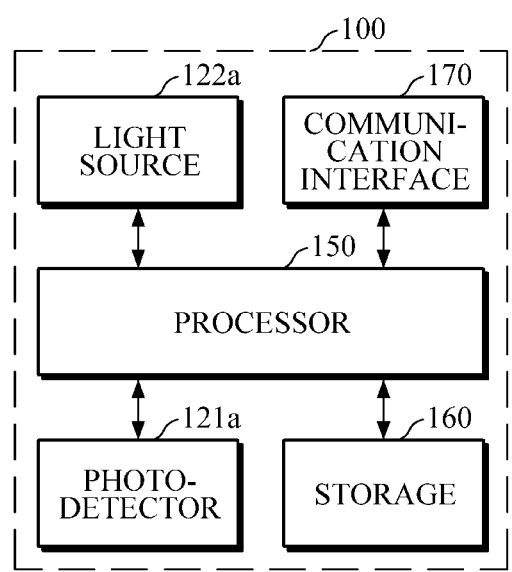
FIG. 13 is a diagram illustrating a control configuration of an assembly for measuring bio-information.

FIG. 13 is a diagram illustrating a control configuration of an assembly for measuring bio-information.

Referring to FIG. 13, an assembly 100 for measuring bio-information may include a storage 160 and a communication interface 170 that are associated with the processor 150. In this case, the assembly 100 for measuring bio-information is applicable to a wearable device, such as eyeglasses on which the storage 160 and the communication interface 170 are not mounted.

The storage 160 may store programs or instructions for the operation of the processor 150, and may store data input to the processor 150 and data output from the processor 150. In addition, the storage 160 may store data processed by the processor 150 and data for data processing by the processor 150 such as, for example, a bio-information estimation model, and the like. The processor 150 controls the driving of a light source 122a, and processes a signal received from a photodetector 121a.

The communication interface 170 may communicate with an external device. For example, the communication interface 170 may transmit data processed by the processor 150 or processing result data of the processor 150 to the external device, or may receive various types of data for measuring a bio-signal and/or estimating bio-information from the external device. When the electronic device includes the processor 150, the storage 160, and the communication interface 170, the processor 150, the storage 160, and the communication interface 170 of the assembly 100 for measuring bio-information may be omitted.

Figure 14:
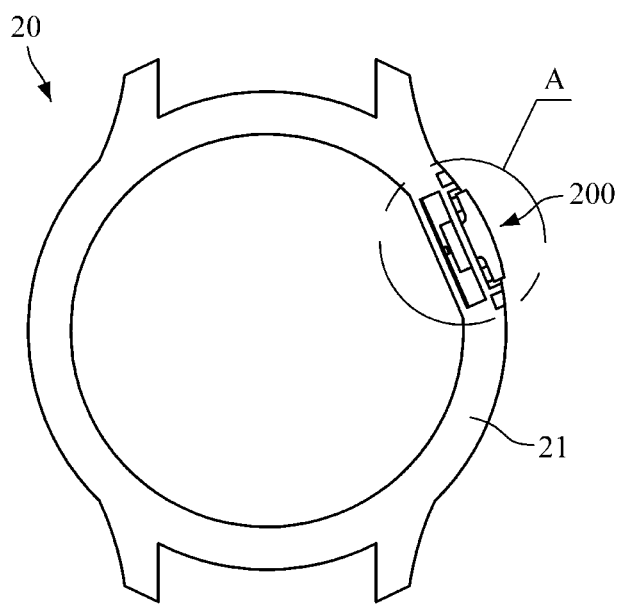
FIG. 14 is a cross-sectional view illustrating an example in which an assembly for measuring bio-information according to an example embodiment is applied to an electronic device.
Figure 15:
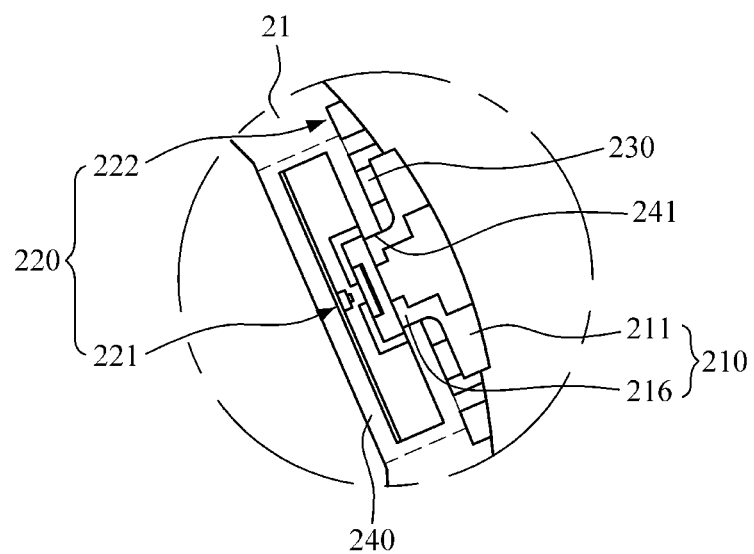
FIG. 15 is a partial cross-sectional view illustrating an area A shown in FIG. 14.
Figure 16:
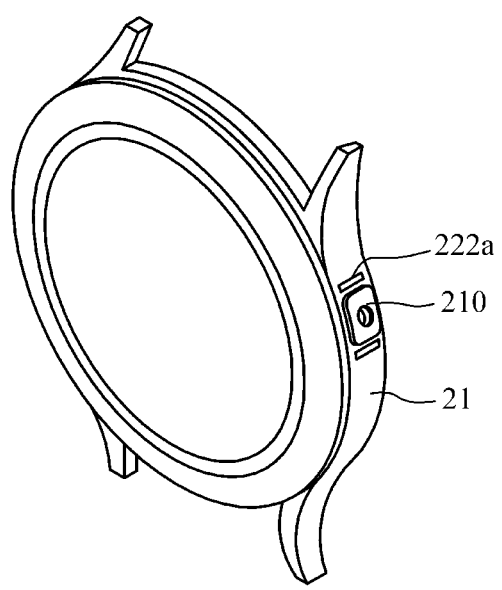
FIG. 16 is a perspective view of FIG. 14.

FIG. 14 is a cross-sectional view illustrating an example in which an assembly for measuring bio-information according to an example embodiment is applied to an electronic device. FIG. 15 is a partial cross-sectional view illustrating an area A shown in FIG. 14. FIG. 16 is a perspective view of FIG. 14.

Referring to FIGS. 14 to 16, an assembly 200 for measuring bio-information according to an example embodiment includes a finger contact interface 210, a bio-sensor 220, a force sensor 230, and a support 240. The finger contact interface 210, the bio-sensor 220, and the force sensor 230 according to the present example embodiment may be configured in the same manner as the finger contact interface 110, the bio-sensor 120, and the force sensor 130 as described above.

The support 240 is formed on a frame of an electronic device. The electronic device may be one of a wearable device and a mobile device. For example, when the electronic device is a smartwatch 20, the support 240 may be integrally made of the same material as a frame 21 of the smartwatch 20.

The support 240 may include a guide hole 241 through which a part of the finger contact interface 210 such as, for example, an interface shaft 216 protruding from the interface body 211, is inserted, thereby linearly guiding the movement of the finger contact interface 210. The guide hole 241 has the same shape as the outer circumferential shape of the interface shaft 216. An inner surface of the guide hole 241 has a surface roughness that enables a smooth sliding with respect to the interface shaft 216.

The support 240 may have a level of strength that prevents the support 240 from deforming due to the contact force of the finger contact interface 210 transmitted through the force sensor 230. The support 240 may be made of a high-strength plastic material with a strength of 0.5 GPa or greater. The support 240 may have an inner space formed to communicate with the guide hole 241. The light receiver 221 may be accommodated in an inner space of the support 240 to receive light reflected from the finger tissue in contact with the finger contact interface 210.

The light emitter 222 may be mounted in the electronic device such as, for example, the smartwatch 20, to emit light to the tissue of the finger 10 in contact with the finger contact interface 210. The light emitter 222 may be disposed around the finger contact interface 210 exposed from the smartwatch 20 and be mounted on the frame 21 of the smartwatch 20.

Accordingly, the light emitter 222 may emit light to the tissue of the finger in contact with the finger contact interface 210. The light emitter 222 may include a pair of light sources 222a symmetrically disposed around the finger contact interface 210, or include three or more light sources 222a arranged in a circle along a periphery of the finger contact interface 210.

Figure 17:
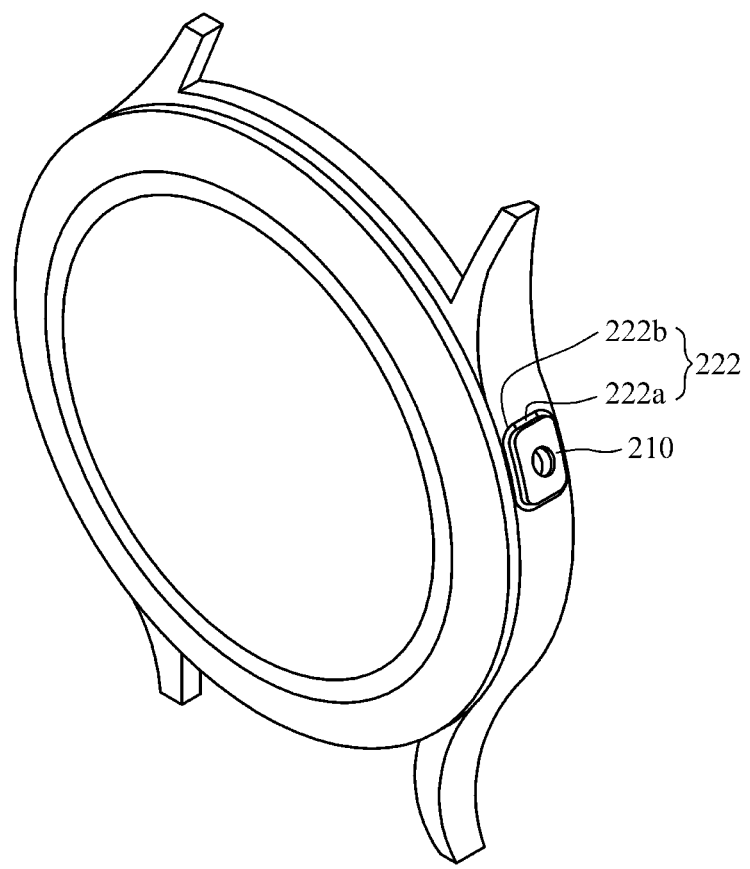
FIG. 17 is a perspective view illustrating another example of a light emitter of FIG. 16.

In another example, as illustrated in FIG. 17, the light emitter 222 may include a light source 222a mounted around the finger contact interface 210 and a light diffusion member 222b arranged along a periphery of the finger contact interface 210 to diffuse light emitted from the light source 222a. Alternatively, the light emitter 222 may be mounted on the finger contact interface 210.

The processor 150 may estimate the user's bio-information based on a signal received from the bio-sensor 220 and a signal received from the force sensor 230, and display the estimation result on a display 22 of the smartwatch 20.

Figure 18:
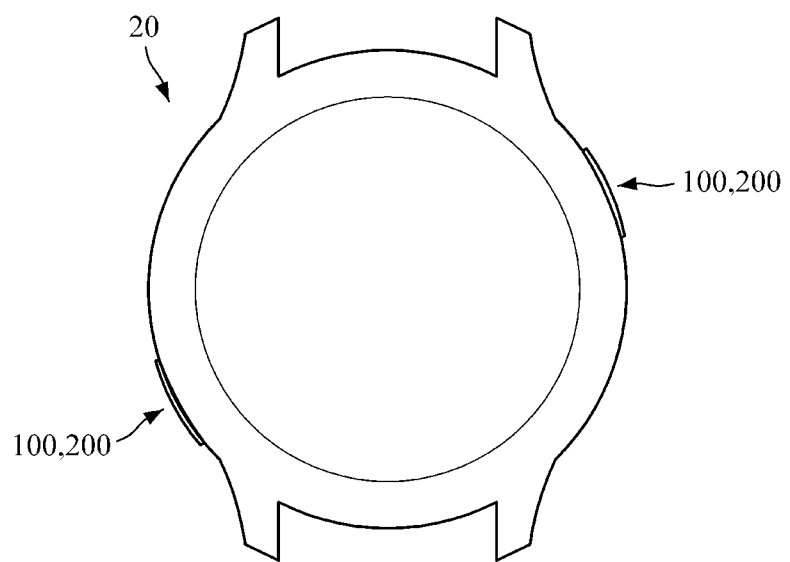
FIG. 18 is a perspective view illustrating another example in which an assembly for measuring bio-information is applied to a smartwatch.

FIG. 18 is a perspective view illustrating another example in which an assembly for measuring bio-information is applied to a smartwatch.

Referring to FIG. 18, two assemblies 100/200 for measuring bio-information may be mounted on both sides of a frame 21 of a smartwatch 20. A user may simultaneously press the assemblies 100/200 for measuring bio-information with a thumb and an index finger, thereby allowing the assemblies 100/200 for measuring bio-information to simultaneously measure bio-information. The assemblies 100/200 for measuring bio-information may be applied to buttons of the smartwatch 20.

Figure 19:
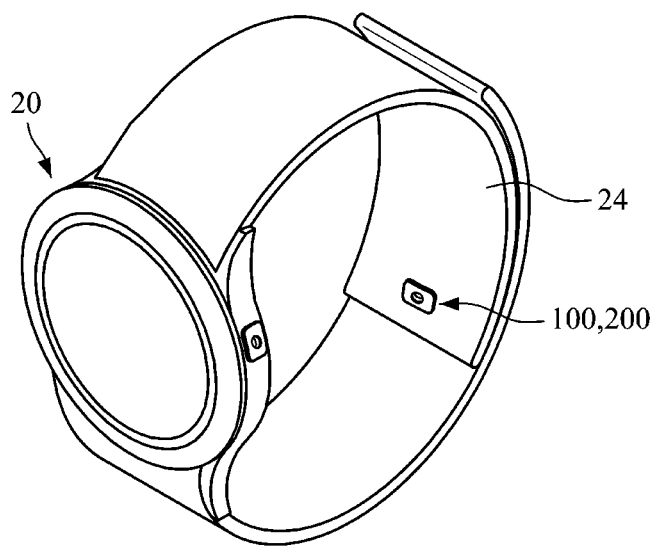
FIG. 19 is a perspective view illustrating still another example in which an assembly for measuring bio-information is applied to a smartwatch.

FIG. 19 is a perspective view illustrating still another example in which an assembly for measuring bio-information is applied to a smartwatch.

Referring to FIG. 19, the assembly 100/200 for measuring bio-information may be mounted on a strap 24 of a smartwatch 20. A user may wear the smartwatch 20 by wrapping the strap 24 around a wrist so that the assembly 100/200 for measuring bio-information is pressed by the wrist and thus can measure bio-information from an aorta radialis. In addition, the user may press the assembly 100/200 for measuring bio-information with a finger while the strap 24 is released from the wrist so that the assembly 100/200 for measuring bio-information can measure bio-information from the finger.

Figure 20:
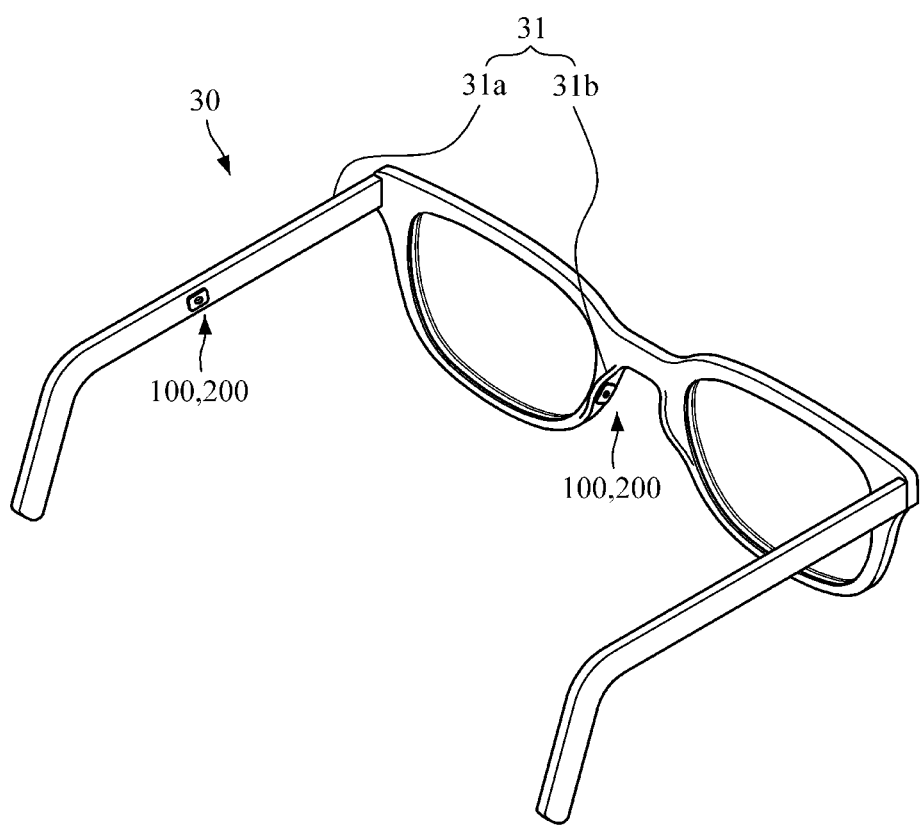
FIG. 20 is a perspective view illustrating an example in which an assembly for measuring bio-information is applied to eyeglasses.

FIG. 20 is a perspective view illustrating an example in which an assembly for measuring bio-information is applied to eyeglasses.

Referring to FIG. 20, the assembly 100/200 for measuring bio-information may be mounted on a frame 31 of eyeglasses 30. The assembly 100/200 for measuring bio-information may be mounted on a temple frame 31*a* of the eyeglasses 30. A user wearing the eyeglasses 30 may press the temple frame 31*a* so that the assembly 100/200 for measuring bio-information is pressed by the temple and can thus measure bio-information from a superficial temporal artery.

In another example, the assembly 100/200 for measuring bio-information may be mounted on a nose bridge frame 31*b* of the eyeglasses 30. The user wearing the eyeglasses 30 may press the nose bridge frame 31*b* so that the assembly 100/200 for measuring bio-information is pressed by the nose and thus can measure bio-information from an angular artery. Here, the eyeglasses 30 may be smart glasses.

As described above, by being applied to the smartwatch 20 or the eyeglasses 30, the assembly 100/200 for measuring bio-information can easily and conveniently measure the user's bio-information. The assembly 100/200 for measuring bio-information may be applied not only to wearable devices and mobile devices, but also to terminals, such as desktop computers, notebook computers, or the like, and medical devices. Alternatively, various modifications may be made such that the assembly 100/200 for measuring bio-information is implemented as an independent device.

Although example embodiments have been described above, it should be understood that various modifications may be made. For example, suitable results may be achieved if the described techniques are performed in a different order and/or if components in a described assembly, system, architecture, device, or circuit are combined in a different manner and/or replaced or supplemented by other components or their equivalents. Accordingly, other implementations are within the scope of the following claims.

What is claimed is:

1. An assembly for measuring bio-information, the assembly comprising:
   a finger contact interface configured to be actuated based on a contact force applied by a finger of a user to the finger contact interface, the finger contact interface comprising an interface body configured to contact the finger of the user on a first side of the interface body;
   a bio-sensor configured to measure the bio-information of the user based on the finger being in contact with the finger contact interface;
   a force sensor configured to measure the contact force of the finger applied to the finger contact interface; and
   a support configured to guide movement of the finger contact interface and support the force sensor against the finger contact interface,
   wherein the force sensor is provided between an outer surface of the support and a second side of the interface body opposite the first side of the interface body,
   wherein the bio-sensor comprises:
      a light emitter external to the support and provided in the finger contact interface, the light emitter configured to emit light to a tissue of the finger in contact with the finger contact interface; and
      a light receiver provided within the support and configured to receive light reflected from an irradiated tissue of the finger in contact with the finger contact interface, the irradiated tissue being irradiated from light emitted from the light emitter,
   wherein the finger contact interface comprises a light path part that extends from the light emitter to the light receiver provided within the support, and
   wherein the light path part comprises a first portion having a first width and that is external to the support, a second portion having a second width less than the first width and that is both external and internal to the support, and a third portion having a third width that is less than the second width and that is internal to the support.

2. The assembly of claim 1, wherein the support comprises a guide hole through which a part of the finger contact interface is inserted, the guide hole being configured to linearly guide the movement of the finger contact interface.

3. The assembly of claim 2, wherein the finger contact interface comprises:
   an interface shaft having a cross-sectional area that is smaller than a cross-sectional area of the interface body, the interface shaft protruding from a second side of the interface body and being configured to move linearly within the guide hole of the support.

4. The assembly of claim 3, wherein at least one force sensor is disposed around a periphery of the guide hole of the support, and faces the interface body.

5. The assembly of claim 1, wherein the finger contact interface comprises a position guide part configured to guide a position of the finger.

6. The assembly of claim 1, wherein the finger contact interface comprises a non-slip part configured to reduce slippage of the finger in contact with the finger contact interface.

7. The assembly of claim 1, further comprising a processor configured to estimate the bio-information of the user based on a first signal received from the light receiver and a second signal received from the force sensor.

8. The assembly of claim 1, wherein the light receiver comprises:
- a photodetector mounted on the support;
- a lens configured to collect incident light and transmit the incident light to the photodetector; and
- an optical filter configured to receive the incident light and pass light of a specific wavelength range to the photodetector.

9. The assembly of claim 8, wherein the photodetector is an image sensor.

10. The assembly of claim 9, further comprising a processor configured to identify the user by acquiring fingerprint information of the user based on a signal received from the image sensor.

11. The assembly of claim 1, wherein the light emitter comprises:
- a light source mounted on the finger contact interface; and
- a light diffusion member configured to diffuse light emitted from the light source.

12. The assembly of claim 1, wherein the bio-sensor comprises an electrode configured to measure at least one of a bio-impedance and an electrocardiogram by contacting the finger through the finger contact interface.

13. The assembly of claim 1, wherein the bio-sensor comprises a temperature sensor configured to measure a temperature signal of the finger in contact with the finger contact interface.

14. An assembly for measuring bio-information, the assembly comprising:
- a finger contact interface configured to be actuated based on a contact force applied by a finger of a user to the finger contact interface, the finger contact interface comprising an interface body configured to contact the finger of the user on a first side of the interface body;
- a bio-sensor configured to measure the bio-information of the user based on the finger being in contact with the finger contact interface;
- a force sensor configured to measure the contact force of the finger applied to the finger contact interface; and
- a support formed on a frame of an electronic device, and that is configured to guide movement of the finger contact interface and support the force sensor against the finger contact interface,
- wherein the force sensor is provided between an outer surface of the support and a second side of the interface body opposite the first side of the interface body,
- wherein the bio-sensor comprises:
  - a light emitter external to the support and provided in the finger contact interface, the light emitter configured to emit light to a tissue of the finger in contact with the finger contact interface; and
  - a light receiver provided within the support and configured to receive light reflected from an irradiated tissue of the finger in contact with the finger contact interface, the irradiated tissue being irradiated from light emitted from the light emitter,
- wherein the finger contact interface comprises a light path part that extends from the light emitter to the light receiver provided within the support, and
- wherein the light path part comprises a first portion having a first width and that is external to the support, a second portion having a second width less than the first width and that is both external and internal to the support, and a third portion having a third width that is less than the second width and that is internal to the support.

15. The assembly of claim 14, further comprising a processor configured to:
- estimate the bio-information of the user based on a first signal received from the light receiver and a second signal received from the force sensor; and
- control a display of the electronic device to display a result of the estimation.

16. The assembly of claim 14, wherein the electronic device is one of a wearable device and a mobile device.

17. An assembly for measuring bio-information of a user, the assembly comprising:
- a contact interface configured to move based on a contact force applied by the user, the contact interface comprising an interface body configured to contact the user on a first side of the interface body;
- a first sensor configured to measure the bio-information of the user based on the contact interface being in contact with the user;
- a second sensor configured to measure the contact force applied by the user to the contact interface; and
- a support configured to guide movement of the contact interface,
- wherein a first surface of the second sensor is provided on the contact interface, and a second surface of the second sensor is provided on the support,
- wherein the second sensor is provided between an outer surface of the support and a second side of the interface body opposite the first side of the interface body,
- wherein the first sensor comprises:
  - a light emitter external to the support and provided in the contact interface, the light emitter configured to emit light to a tissue of the user applying the contact force; and
  - a light receiver provided within the support and configured to receive light reflected from an irradiated tissue of the user applying the contact force, the irradiated tissue being irradiated from light emitted from the light emitter,
- wherein the contact interface comprises a light path part that extends from the light emitter to the light receiver provided within the support, and
- wherein the light path part comprises a first portion having a first width and that is external to the support, a second portion having a second width less than the first width and that is both external and internal to the support, and a third portion having a third width that is less than the second width and that is internal to the support.

* * * * *